United States Patent
Lobbert et al.

(10) Patent No.: US 10,267,764 B2
(45) Date of Patent: Apr. 23, 2019

(54) POTENTIOMETRIC SENSOR APPARATUS

(71) Applicant: Endress + Hauser Conducta Gesellschaft fur Mess- und Regeltechnik mbH + Co. KG, Gerlingen (DE)

(72) Inventors: Andreas Lobbert, Waldheim (DE); Michael Hanko, Dresden (DE); Katrin Scholz, Bobritzsch (DE)

(73) Assignee: Endress + Hauser Conducta GmbH + Co. KG, Gerlingen (DE)

( * ) Notice: Subject to any disclaimer, the term of this patent is extended or adjusted under 35 U.S.C. 154(b) by 981 days.

(21) Appl. No.: 13/861,664

(22) Filed: Apr. 12, 2013

(65) Prior Publication Data

US 2013/0270125 A1  Oct. 17, 2013

(30) Foreign Application Priority Data

Apr. 17, 2012 (DE) .................. 10 2012 103 341

(51) Int. Cl.
 *G01N 27/416* (2006.01)
 *G01N 27/36* (2006.01)
 *G01N 27/403* (2006.01)

(52) U.S. Cl.
 CPC ......... *G01N 27/4163* (2013.01); *G01N 27/36* (2013.01); *G01N 27/4035* (2013.01)

(58) Field of Classification Search
 CPC ........... G01N 27/4163; G01N 27/4035; G01N 27/36; G01N 27/30; G01N 27/33;
 (Continued)

(56) References Cited

U.S. PATENT DOCUMENTS 3,635,212 A * 1/1972 Watanabe .......... G01N 27/3335
 204/420
4,632,746 A * 12/1986 Bergman ............. G01N 27/404
 204/415

(Continued)

FOREIGN PATENT DOCUMENTS

CN 87106356 A 6/1988
CN 101529236 A 9/2009

(Continued)

OTHER PUBLICATIONS

German Search Report, Munich, dated Dec. 10, 2012.

(Continued)

*Primary Examiner* — Gurpreet Kaur
(74) *Attorney, Agent, or Firm* — Christopher R. Powers; PatServe

(57) ABSTRACT

A potentiometric sensor apparatus, comprising: a measuring half-cell having a measuring membrane; a reference half-cell; and a measurement circuit for registering a potential difference between the measuring half-cell and the reference half-cell. The measuring membrane has, covering at least one portion of the measuring membrane during dry storage of the sensor apparatus, a coating, which is embodied, upon immersion of at least one immersion region of the sensor apparatus (which region comprises the measuring membrane and is intended for immersion in a measured medium) in a liquid, especially a water containing liquid, in the case of continued contact with the liquid, to dissolve, at least partially, off of the measuring membrane.

21 Claims, 6 Drawing Sheets

(58) Field of Classification Search
CPC .. G01N 27/31; G01N 27/333; G01N 27/4166; G01N 27/4167; G01N 27/301; G01N 27/302; G01N 27/3335; G01N 27/416; G01N 27/4117; C12M 41/26; C12M 41/28
See application file for complete search history.

(56) References Cited

U.S. PATENT DOCUMENTS

| | | | |
|---|---|---|---|
| 4,959,138 A * | 9/1990 | Brinkmann | G01N 27/30 204/401 |
| 5,016,201 A | 5/1991 | Bryan | |
| 5,472,590 A * | 12/1995 | Yamashita | G01N 27/414 204/403.13 |
| 5,911,862 A * | 6/1999 | Chan | G01N 27/414 204/416 |
| 7,176,692 B2 | 2/2007 | Adami | |
| 7,674,254 B2 | 3/2010 | Baumfalk | |
| 7,704,359 B2 | 4/2010 | Sovrano | |
| 2009/0211924 A1* | 8/2009 | West | G01N 27/4035 205/787.5 |
| 2010/0025235 A1* | 2/2010 | Nishio | C03B 9/31 204/282 |
| 2010/0209811 A1* | 8/2010 | Barnwell | H01M 8/0273 429/483 |
| 2010/0276303 A1 | 11/2010 | Fujiwara | |
| 2010/0301060 A1 | 12/2010 | Bernard | |
| 2011/0033917 A1* | 2/2011 | Trapp | G01N 33/54373 435/288.7 |
| 2012/0118762 A1* | 5/2012 | Bakker | G01N 27/333 205/789 |
| 2012/0144894 A1* | 6/2012 | Trapp | G01N 35/00693 73/1.06 |
| 2012/0152765 A1* | 6/2012 | Trapp | G01N 27/4163 205/787.5 |
| 2015/0027887 A1* | 1/2015 | Lee | G01N 27/286 204/406 |
| 2016/0137541 A1* | 5/2016 | Zilly | C03B 9/41 65/29.11 |
| 2017/0157571 A1* | 6/2017 | Thomas | B01D 69/144 |

FOREIGN PATENT DOCUMENTS

| | | |
|---|---|---|
| DE | 4207845 C1 | 9/1993 |
| DE | 19539763 A1 | 4/1997 |
| DE | 102005033727 A1 | 1/2007 |
| DE | 102006005533 A1 | 8/2007 |
| DE | 102008055107 A1 | 1/2010 |
| DE | 102010063031 A1 | 6/2012 |
| EP | 0270751 A3 | 6/1988 |
| EP | 0520443 A2 | 12/1992 |
| EP | 1548428 A1 | 6/2005 |
| EP | 1564549 A1 | 8/2005 |
| EP | 1610120 B1 | 12/2005 |
| EP | 1610120 B1 | 9/2009 |
| WO | 2009059645 A1 | 5/2009 |
| WO | 2010072601 A1 | 7/2010 |

OTHER PUBLICATIONS

Jeonghan Ha, Steven M. Martin, Youngho Jeon, In Jun Yoon, Richard B. Brown, Hakhyun Nam, Geun Sig Cha, "A Polymeric Junction Membrane for Solid-State Reference Electrodes", In: Analytica Chimica Acta, 549, 2005.

German Search Report, German Patent Office, Munich, dated Jun. 5, 2013.

* cited by examiner

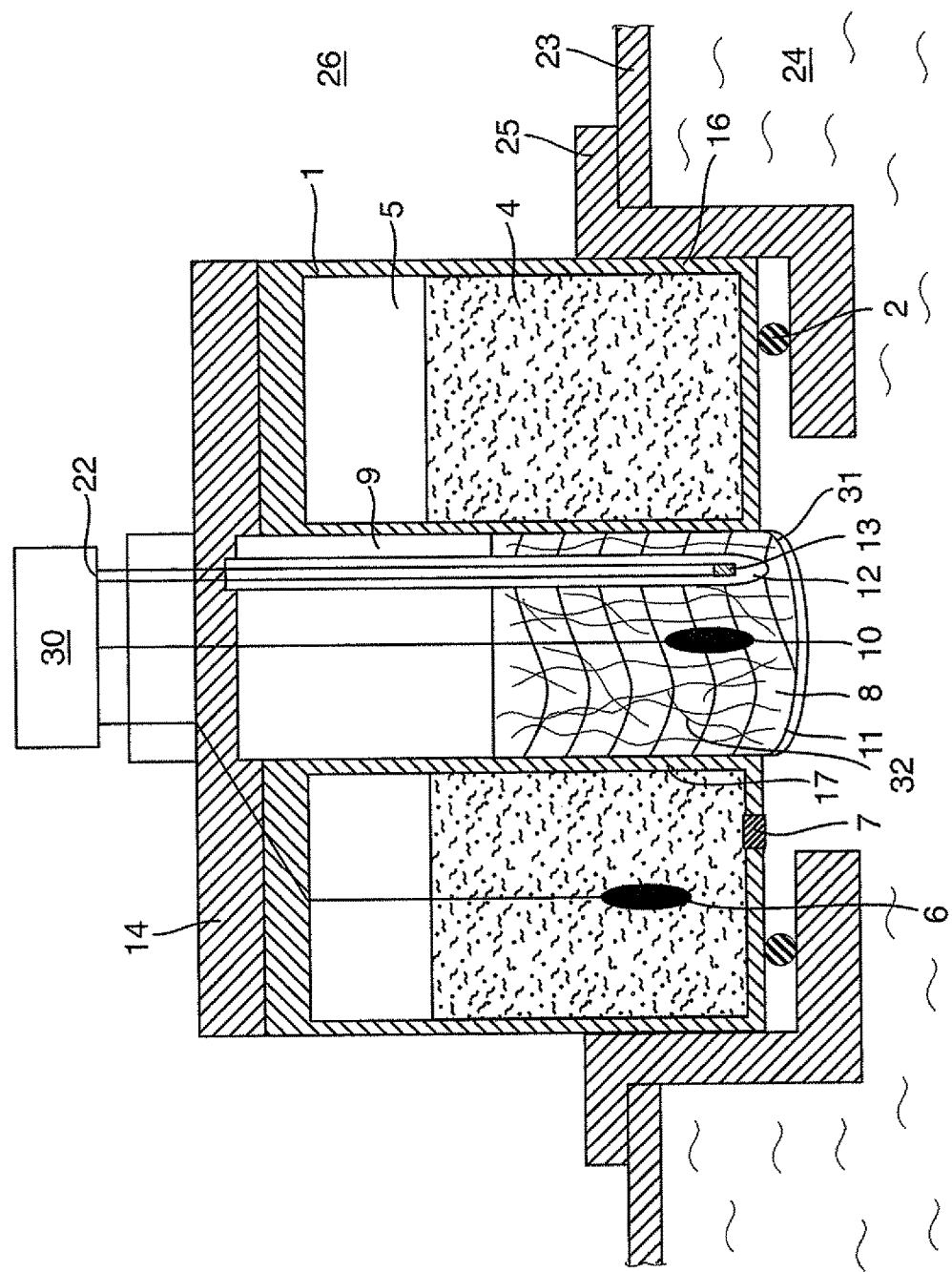

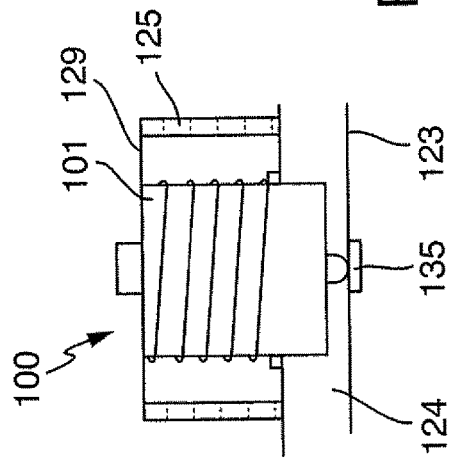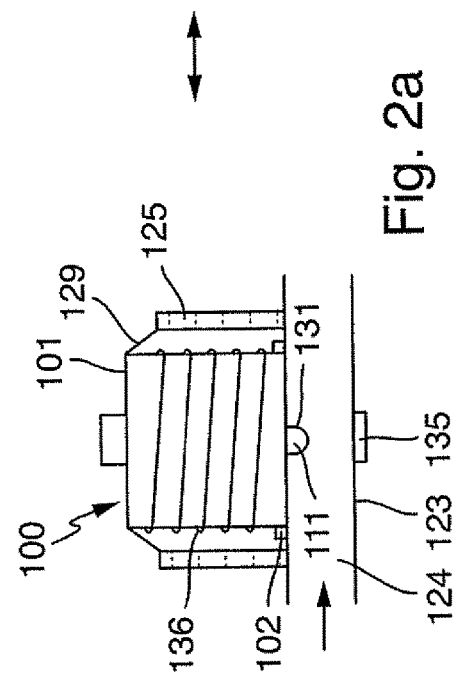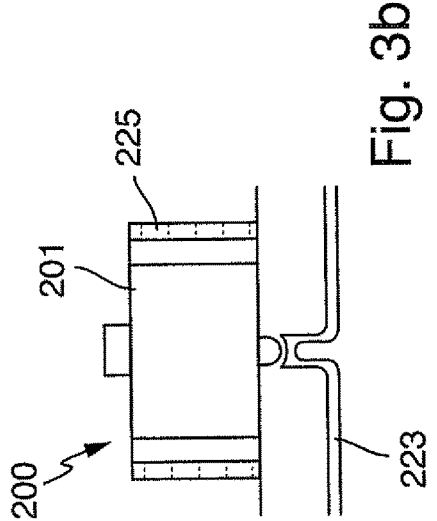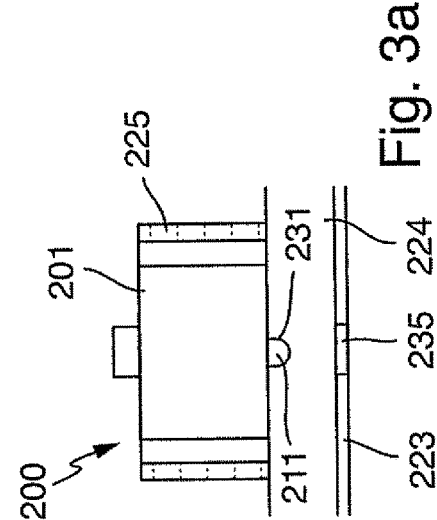

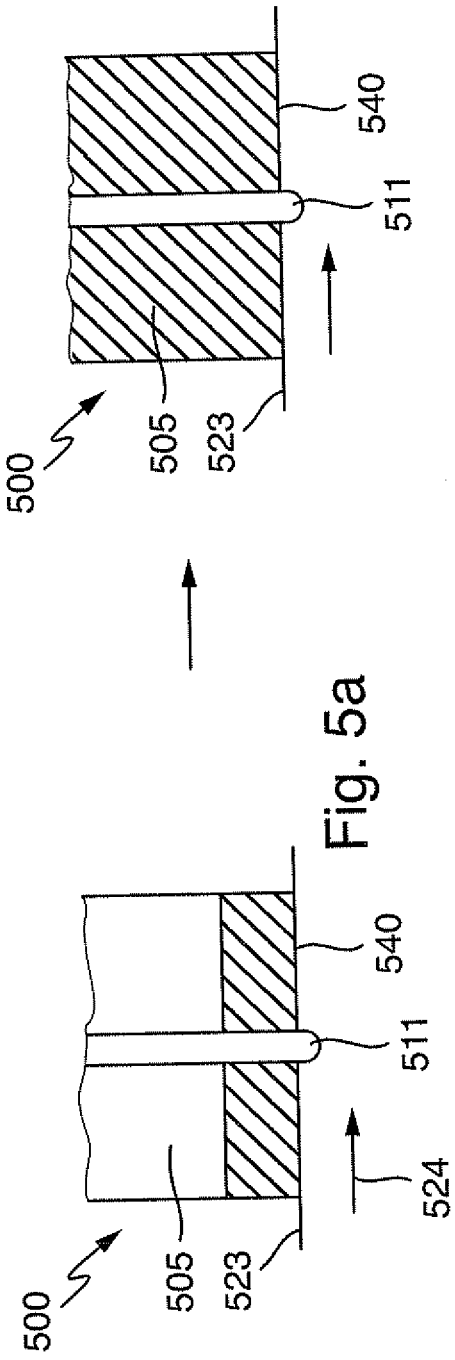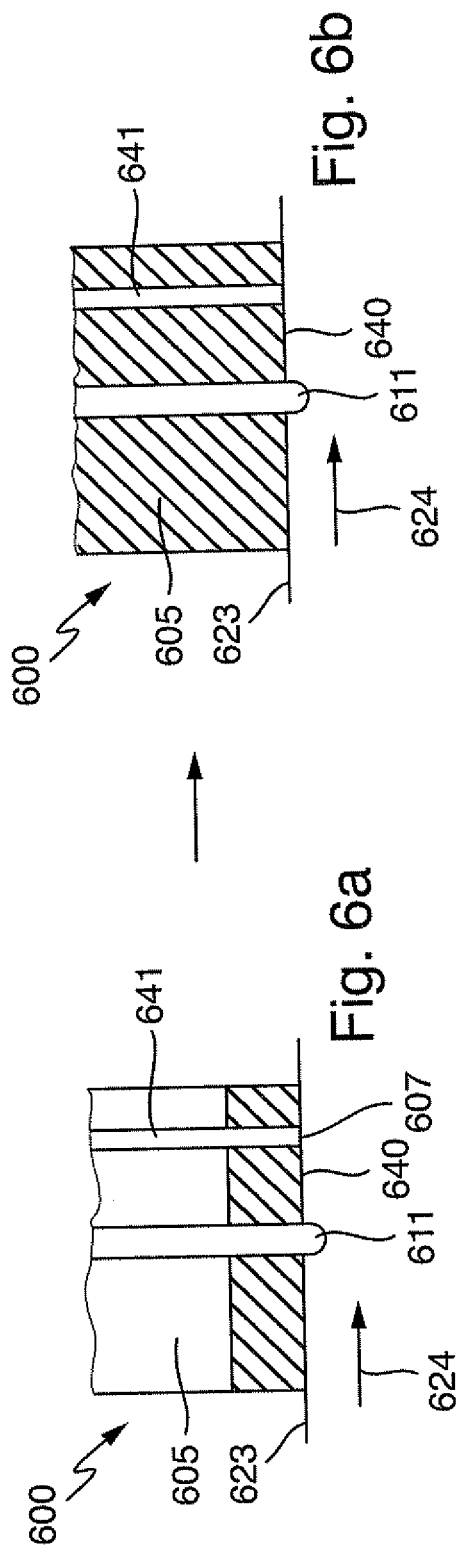

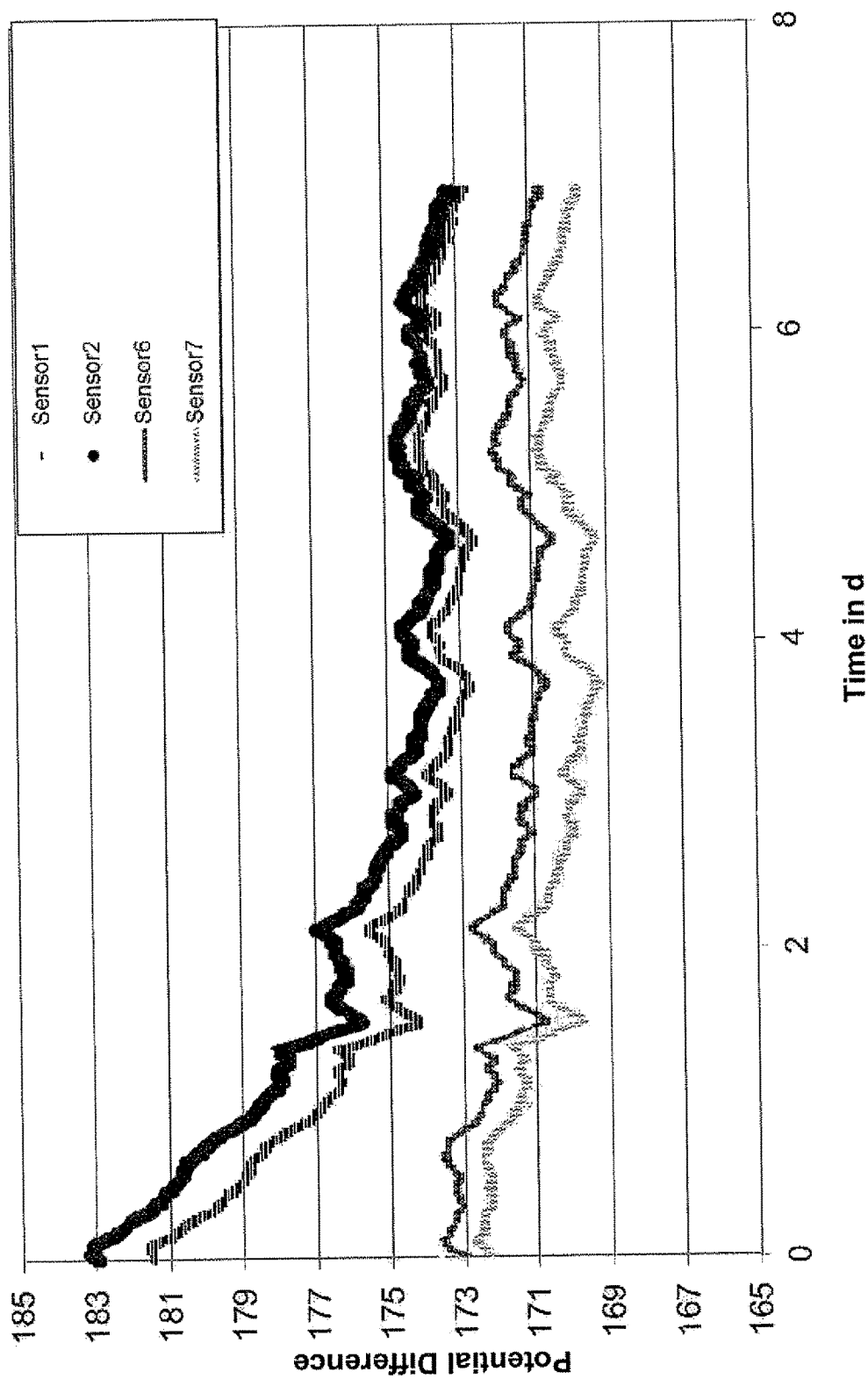

POTENTIOMETRIC SENSOR APPARATUS

TECHNICAL FIELD

The invention relates to a potentiometric sensor apparatus, especially one for registering a measured variable of a liquid, measured medium. Such measured variable can be, for example, the pH-value of the measured medium or concentration of certain chemical substances dissolved in the measured medium, for example, certain ions. Such sensor apparatuses are applied, for example, in laboratory applications, in process measurements technology or in environmental analytics.

BACKGROUND DISCUSSION

Potentiometric sensors comprise a measuring half-cell and a reference half-cell. The measuring half-cell includes a sensitive element, which is frequently embodied as a measuring membrane, on which a potential occurs, dependent on the measured variable. Used as reference half-cell can be, for example, a reference electrode of second type known per se, e.g. a silver/silver chloride, reference electrode, which provides a stable reference potential independent of the measured variable. The determining of the measured variable occurs based on the registering of a potential difference occurring between the measuring half-cell and the reference half-cell in contact with the measured medium. Examples of such potentiometric sensors are so-called ion-selective electrodes (ISEs).

A special case of an ion-selective electrode for determining the pH-value of a liquid is the glass electrode for pH-measurements. The glass electrode includes a housing, in which a measuring half-cell chamber is formed, which is sealed on an end by a pH-sensitive glass membrane. Accommodated in the measuring half-cell chamber is an inner electrolyte, which, as a rule, comprises a pH buffer system. The glass membrane thus contacts the internal electrolyte with its inner surface facing the measuring half-cell chamber. For performing pH-measurements, the outer surface of the glass membrane facing away from the measuring half-cell chamber is brought in contact with a measured medium. In contact with a water containing medium, the glass membrane forms a gel layer. In such case, there occurs on the interface between the membrane glass and the aqueous medium a dissociation, in the case of which alkali ions of the glass are replaced by protons from the aqueous medium, so that a large number of hydroxyl groups are formed in the gel layer. In measurement operation of the electrode, this occurs both on the inner surface contacting the inner electrolyte as well as also on the outer surface of the membrane contacting the measured medium. Depending on the pH-value of the measured medium, $H^+$ ions diffuse out from the gel layer or into the gel layer. Since the inner electrolyte has a constant pH-value, there thus results across the membrane a potential difference dependent on the pH-value of the measured medium. For achieving a stable potential on the glass surface and for assuring a fast response, i.e. a short time span between immersion of the measuring membrane in the measured medium and the reaching of a value of the membrane potential fluctuating only within a predetermined error/tolerance range, the gel layer must be completely formed. After a drying out of, or other damage to, the gel layer, this response time can lengthen significantly, until even a number of hours can be required for reaching a constant, measured value.

A reference electrode of second type, such as the silver/silver-chloride electrode, includes, formed in a housing, a reference half-cell chamber, which contains a defined electrolyte solution. This inner electrolyte must contact the measured medium, in order to be able to perform a measurement. Such contact is via a liquid junction, which can be produced, for example, by a passageway through the housing wall, by a porous diaphragm or by a gap. Extending into the inner electrolyte is a potential sensing element. The potential of the reference electrode is defined by the reference electrolyte and the potential sensing element. In the case of a silver/silver-chloride electrode, the inner electrolyte is, for example, an aqueous solution of high chloride concentration, as a rule, a 3 molar, or saturated, KCl solution, and the potential sensing element is a chlorided silver wire.

Since the potential of the reference half-cell is essentially pH-value independent and can be assumed to be constant as a function of time, the potential difference registerable between a potential sensing element extending into the inner electrolyte of the measuring half-cell and the potential sensing element of the reference half-cell by means of a measurement circuit is a measure for the potential difference between the inner surface of the measuring membrane and the outer surface of the measuring membrane dependent on the pH-value of the measured medium, and, thus, a measure for the pH-value of the measured liquid.

Such potentiometric sensors can be embodied as a measuring chain with two separated, in each case, rod-shaped, housings for measuring- and reference half-cells. Frequently, the two half-cells are, however, combined into a single-rod measuring chain, or combination electrode, which has a single housing, in which are formed two chambers separated from one another, wherein one chamber serves as measuring half-cell chamber and the other as reference half-cell chamber.

Both half-cells should, not only during measurement operation, but also during storage, be sitting in a liquid, for example, in a buffer solution or in a salt solution. In the case of dry storage of the sensor, it is possible, on the one hand, that the inner electrolyte of the reference half-cell can leak out through the liquid junction, or dry out, while, on the other hand, the gel layer of the measuring half-cell can dry out. In order to be able to get a dry stored, potentiometric pH-sensor back in operation, the measuring half-cell must be placed at least 12 hours in a water containing buffer- or electrolyte solution, in order to build anew a gel layer formed sufficiently for assuring a fast response. Similar effects arise also in the case of other ion-selective electrodes, in the case of which glass is applied as sensitive material (e.g. thus in the case of Na selective glasses).

Pharmaceutical, chemical, biological, biochemical or biotech processes are, in increasing measure, performed in single-use containers serving as the process container (these are referred to as 'disposables', or disposable bioreactors). Such single-use containers can include, for example, flexible containers, e.g. bags, hoses or fermenters, or bioreactors. Bioreactors or fermenters frequently have supply and drain lines, which can be embodied, for example, as hoses or flexible tubes. Inserted in the supply and drain lines can also be rigid tubular pieces or pipes. After terminating a process, the single-use containers can be disposed of. In this way, complex cleaning- and sterilization procedures are avoided. Especially through the use of single use-containers, the risk of cross contamination is avoided, and therewith, process safety increased.

The processes performed in the single-use containers operate in a closed system, i.e. without connection to the environment outside of the single-use container. Since, frequently, sterile conditions are required, the single-use containers must be sterilized before introduction of the process media. To this end, in biochemical, biological, biotechnological and pharmaceutical applications, frequently gamma- or beta radiation is used. Also, while the processes are running in a single-use container, the penetration of impurities, especially of germs, from the environment into the interior of the process container must be prevented, in order not to degrade, or corrupt, the process.

Potentiometric sensors to be used in such a single-use containers can ideally be installed fixedly in a wall of the container already before the sterilization of the container and remain there for the duration of both storage and later use. Such sensors, or containers with such sensors, are described, for example, in German patent application DE 10 2010 063031 A1. While the actual time of use of the single-use container amounts, as a rule, only to a few days up to a number of weeks, storage times of the container with the already installed sensors can be in the order of magnitude of one or more years. Dry storage of the sensor installed in the container brings about, according to the state of the art, the already described disadvantages of lengthened response time. Storage of the sensor in a liquid during sterilization or during a warehousing period is cumbersome and even impractical.

Known from WO 2009/059645 A1 is, for example, a single-use container with integrated pH-sensor, which can also be sterilized together. The pH-sensitive membrane is stored in a compartment containing a pH-stable, storage solution. The storage solution serves also as calibration solution for a one point calibration. For performing measurements, the compartment is opened to the process container in manner not described in greater detail.

Optical, or optochemical, sensors for single use measurements are likewise known.

Also, known from DE 10 2010 001 779 A1 is a calibratable sensor unit for a single use, reaction container, in which case the sensitive element is stored with calibration means, e.g. a buffer solution, before start-up within a compartment closed from the process container by a membrane. Disadvantageous in this embodiment is that the flexible isolating membrane can be damaged during transport or during storage of the reaction container.

SUMMARY OF THE INVETNION

An object of the invention is to provide a potentiometric sensor apparatus, which, after dry storage over a longer period of time, can be placed in operation for performing measurements faster than the potentiometric sensors known from the state of the art.

This object is achieved by a potentiometric sensor apparatus, comprising:
a measuring half-cell having a measuring membrane,
a reference half-cell, and
a measurement circuit for registering a potential difference between the measuring half-cell and the reference half-cell, wherein the measuring membrane has, covering at least one portion of the measuring membrane during dry storage of the sensor apparatus, a coating, which is embodied, upon immersion of at least one immersion region of the sensor apparatus (which region comprises the measuring membrane and is intended for immersion in a measured medium) in a liquid, especially a water containing liquid, in the case of continued contact with the liquid, to dissolve, at least partially, off of the measuring membrane.

Experiments have shown that the coating covering the at least one portion of the measuring membrane assures a faster response of the sensor apparatus upon start-up after a longer dry storage phase compared with conventional dry stored, sensor apparatuses. It is possible that the coating prevents a drying out of the gel layer or at least lessens such and so accelerates the response after a longer dry storage phase. After a dry storage and/or a sterilization with gamma radiation of a total radiation dosage of at least 25 kGy of the sensor apparatus over a predetermined first time span, a second time span from the immersion of the immersion region of the sensor apparatus into the liquid to the reaching of a potential difference constant within a predetermined tolerance range, between the measuring half-cell and the reference half-cell is, consequently, shorter than a second time span from the immersion of the immersion region of the sensor apparatus into the liquid to the reaching of a potential difference constant, within the same predetermined tolerance range, between the measuring half-cell and the reference half-cell after a dry storage and/or a sterilization with gamma radiation of a total radiation dosage of at least 25 kGy of the sensor apparatus during the predetermined first time span without the coating.

In an embodiment of the invention, the measuring membrane in contact with a water containing medium forms a gel layer, wherein the coating shields, or protects and maintains, the gel layer during the dry storage of the sensor apparatus. This is, for example, the case for a measuring membrane embodied in the form of a pH-sensitive, glass membrane provided with a coating of the invention. The gel layer can comprise a large number of hydroxyl groups, wherein the coating is embodied to stabilize at least one part of the hydroxyl groups and/or to transfer protons between coating and measuring membrane for forming hydroxyl groups. For example, the measuring membrane can be pregelled in the manufacture of the sensor apparatus by immersion in a suitable buffer- or electrolyte solution in order to produce a gel layer before applying the coating. The coating applied thereafter can be embodied to stabilize the external gel layer of the measuring membrane, especially its hydroxyl groups. In this embodiment, the measuring membrane thus includes a gel layer covered by the coating. In an alternative manufacturing process, the pregelling of the measuring membrane can be omitted, and the coating applied directly on the dry measuring membrane. In this case, the coating can be embodied to bring about a pregelling of the measuring membrane. The coating in this embodiment contains protons, hydroxyl ions and/or water molecules, so that protons can be exchanged between the coating and the measuring membrane. In this embodiment, the measuring membrane likewise includes a gel layer covered by the coating, wherein, in given cases, the gel layer is thinner than in the earlier described embodiment.

For start-up of the sensor apparatus after a longer time span of dry storage, the immersion region of the sensor apparatus surrounding the measuring membrane can be immersed in a water containing liquid, especially in a water containing measured medium. The material of the coating can be a highly viscous substance clinging to the measuring membrane, or a solid substance, which, in contact with the water-containing liquid, absorbs water and eventually dissolves in the liquid. The coating can, especially in applications for sensor apparatuses, which are used in a container of single use, process technology, be embodied of a material, which retains its functional capabilities despite exposure to gamma radiation. Preferably, a non-toxic material is used, which is suitable for the respective process. For example, the material permitted for the respective process can be a material permitted for the process, preferably an FDA permitted material.

Preferably, here, especially a non-toxic and/or non-cytotoxic material is applied, which is suitable and permitted (e.g. FDA permitted) for the respective process.

Advantageously, the coating can supplementally comprise a calibration means for performing a calibration of the potentiometric sensor apparatus. If the sensor apparatus is for pH measurement, the calibration means can be a pH buffer system. In contact with liquid, for example, the measured medium, the polymeric or oligomeric, high viscosity or solid material or composite of the coating undergoes gelling and forms, by water uptake, a gel containing the buffer system, or a polymeric buffer, which still clings to the measuring membrane, so that a calibration measurement can be performed. Preferably, the speed of dissolution of the coating is small enough that gel containing the buffer or the polymeric buffer dissolves off of the measuring membrane only after a period of time of less than 15 min, preferably less than 5 min, further preferably less than 2.5 min, after the immersion in a water containing liquid.

The coating can preferably comprise a viscous or solid, basic component, especially one or more substances of the group formed by urea, polyurea, polyethelene glycol, polyethylene imine, poly(methacrylic acid), cellulose, polyvinyl alcohol and derivatives thereof. These have a sufficiently slow rate of dissolution from the measuring membrane upon contact with a liquid, especially a water containing liquid, for example, an aqueous, measured medium. Additionally, these substances possess a sufficient stability under gamma irradiation.

The buffer system serving as calibration means can preferably be selected from the group formed by phthalate/phthalic acid, citrate/citric acid, dihydrogen phosphate/phosphoric acid, monohydrogen phosphate/dihydrogen phosphate, monohydrogen phosphate/phosphate, acetic acid/acetate, propionic acid/propionate, tartaric acid/tartrate, succinic acid/succinate, lactic acid/lactate, sorbic acid/sorbate, benzoic acid/benzoate, malic acid/malate, hydrogen carbonate/carbonate.

In an additional embodiment, the coating can comprise, as calibration means for performing a calibration of the potentiometric sensor apparatus, a pH buffer system, which includes at least one water soluble, oligomer- or polymer component, especially an oligomer- or polymer component selected from the group formed of methacrylates and their copolymers, or polymers with organic phosphate groups, such as e.g. ethylene glycol methacrylate phosphate. The coating can comprise supplementally at least one antioxidant, especially a radical interceptor, in order, for example, to capture radicals occurring during gamma irradiation and lessen damaging of the coating and/or the measuring membrane. The antioxidant can preferably be selected from the group formed of silver salts, 2,2,6,6-tetramethyl piperidinyl oxyl (TEMPO), phosphate- or carbonate buffer, rosmarinic acid, citric acid and ascorbic acid.

The measuring half-cell can have a measuring half-cell chamber formed in a housing of the sensor apparatus, sealed by the measuring membrane, and containing an inner electrolyte, which has a water content of less than 90 mass-%, preferably less than 60 mass-%, further preferably less than 30 mass-%. The inner electrolyte is preferably a non-aqueous electrolyte, for example, a polymer electrolyte, which contains a water containing, pH buffer system.

Contained in the measuring half-cell chamber can be an inorganic filler, preferably a hydrophilic, inorganic filler, for example, in the form of a porous body and/or a multiplicity of fibers, especially in form of a fibrous weave or an assembly of fibers, e.g. a felted material, and/or at least one capillary tube, preferably a plurality of capillary tubes, and/or a powder. The fibers of the fibrous weave or of the assembly of fibers have preferably a fiber separation of <100 µm, at least, however, a fiber separation of 0.05 µm. The porous body, the fibers, the capillary tubes and/or the powder can comprise a hydrophilic material, preferably containing aluminum oxide, titanium oxide and/or silicon oxide or a glass containing aluminum oxide, titanium oxide and/or silicon oxide. The filler can serve to transport the inner electrolyte by means of capillary forces, even counter to the force of gravity. This enables an application of the measuring half-cell independently of its installed position, since the filler, independently of the installed position, assures a durable wetting of the inner side of the measuring membrane.

The inner electrolyte can, same as the coating, contain, supplementally, an antioxidant, especially a radical interceptor, in order, for example, to capture radicals occurring during beta- or gamma irradiation and to lessen damaging of the coating and/or the measuring membrane. The antioxidant can be selected from the group formed of silver salts, 2,2,6,6-tetramethyl piperidinyl oxyl (TEMPO), phosphate- or carbonate buffer, rosmarinic acid, citric acid and ascorbic acid.

Extending into the inner electrolyte of the measuring half-cell as potential sensing element can be a metal electrode, especially a chloridized silver wire. The potential sensing element is connected with the measurement circuit in such a manner that the measurement circuit can register a potential difference between the potential sensing element of the measuring half-cell and a potential sensing element of the reference half-cell.

The reference half-cell of the sensor apparatus in an embodiment can have a reference half-cell chamber formed in the housing of the sensor apparatus, and a liquid junction arranged in a wall of the housing within the immersion region of the sensor apparatus, wherein a substance, preferably a dry or low moisture substance, is contained in the reference half-cell chamber, and wherein the reference half-cell is embodied to transport liquid through the liquid junction into the reference half-cell chamber, in order to form a reference electrolyte from the substance contained in the reference half-cell chamber and the liquid transported into the reference half-cell chamber.

This embodiment of the reference half-cell permits dry storage of the reference half-cell and sterilizing of the reference half-cell by means of gamma radiation, since the reference half-cell chamber can in this embodiment be packaged and stored largely dry and, in given cases, gas-free before start-up of the sensor apparatus. Liquid contained in the reference half-cell chamber of conventional reference half-cells of potentiometric sensors can, when exposed to gamma radiation of the dosage typically used for sterilization in the field of the single use, process technology, be ionized, so that, in the presence of water, radicals arise, which, in turn, can enter into other reactions with other materials of the sensor apparatus. This leads to an aging of the reference half-cell, which is disadvantageous for the speed of response of the sensor apparatus. The here described, largely dry and dryly storable, reference half-cell, in the case of which liquid for forming the reference electrolyte is first transported into the reference half-cell chamber upon start-up of the sensor apparatus, avoids this disadvantage.

Furthermore, a leaking out of the reference electrolyte through the liquid junction, such as can occur in the case of liquid- or gel filled reference-half-cells stored over longer periods of time, is prevented. Additionally, a drying of the gel in the region of the liquid junction, such as can occur in the case of gel filled, reference half-cells, can also be prevented. In both cases, through the application of a largely dryly filled reference half-cell, malfunctions of the sensor are lessened.

Contained in the reference half-cell chamber can be an electrolyte salt, e.g. KCl, in the dry state, for example, as fill, in the form of one or more crystals or as a briquette. During transport of liquid into the reference half-cell chamber, the electrolyte salt dissolves in the liquid and so forms an inner electrolyte solution of the reference half-cell.

The reference half-cell can have transport means for the transport of liquid through the liquid junction of the reference half-cell chamber, wherein the transport means are embodied to transport the liquid by means of capillary forces.

The transport means can comprise a dialysis membrane, a porous body and/or fibers, especially a fibrous weave or an assembly of fibers with a fiber separation of <100 µm, preferably <10 µm, and/or at least one capillary tube, preferably a plurality of capillary tubes, and/or a powder.

The porous body, the fibers, the capillary tubes and/or the powder can comprise a hydrophilic material, especially a glass or a ceramic, which preferably contains aluminum oxide and/or titanium oxide and/or silicon oxide. To the extent that a fibrous weave or assembly of fibers is used, the velocity of the liquid transport into the reference half-cell can be influenced by selection of the fiber separation. Preferably used is a fiber separation of less than 10 µm, still more preferably less than 1 µm and most preferably less than 0.1 µm.

If the reference half-cell chamber contains a hydrophilic powder for the transport of the liquid into the reference half-cell chamber, total surface area of the powder is greater than 10 $m^2/g$, preferably greater than 100 $m^2/g$ and still more preferably, greater than 200 $m^2/g$ or even greater than 500 $m^2/g$.

As already mentioned, the transport means for the transport of the liquid through the liquid junction can comprise a dialysis membrane. The terminology 'dialysis membrane' means here a size-filtration membrane, which is porous only for small ions and molecules, especially for water molecules. The driving force for the transport of the liquid by means of the porous body, the fibers or capillary tubes are capillary forces, while the driving force for the transport of water and smaller ions and molecules through the dialysis membrane is a gradient of the chemical potential extending through the membrane.

The dialysis membrane can be formed of a material having an average exclusion volume of less than 50 kDa, preferably less than 20 kDa. Suited are e.g. preferably materials stable under gamma irradiation, for example, a polymer material selected from the group formed of acetylated cellulose derivatives, especially cellulose esters, ethyl cellulose, alkylene oxide/alkyl glycidyl ether copolymers, polyglycols, polymeric epoxides, poly(lactic acid) derivatives, and water insoluble acrylates, such as copolymers based on ethyl acrylate and/or methyl methacrylate.

A suitable membrane can be a polymer membrane, for example, of ethyl cellulose, an alkylene oxide/alkyl glycidyl ether-copolymer, a polymeric epoxide, a poly(lactic acid) derivative or a polyglycol, as well as a protective layer, which can comprise, for example, a cellulose derivative, especially acetylated cellulose derivatives, which can be mono- to trisubstituted, such as e.g. cellulose acetate, cellulose triacetate, cellulose acetate/ethyl carbamate, or cellulose acetate phthlate.

The liquid junction can be embodied as an annular gap, as a pore or as a membrane.

The reference half-cell can include a potential sensing element, which can be embodied, for example, as a chloridized silver wire, and which protrudes inwardly into the reference half-cell chamber, so that, after start-up of the sensor apparatus, it is in contact with the liquid reference electrolyte formed due to the transport of liquid through the liquid junction into the reference half-cell chamber. The potential sensing element is connected with the measurement circuit of the sensor apparatus in such a manner that the measurement circuit can register a potential difference between the potential sensing element of the measuring half-cell and the potential sensing element of the reference half-cell.

The reference half-cell described here can be applied advantageously in combination with the above described measuring half-cell, in order so to provide a potentiometric sensor apparatus, which even after a longer period of dry storage and a sterilizing by means of gamma radiation is, after start-up, clearly faster ready for performing measurements providing a stable measured value than previously possible with potentiometric sensor apparatuses known from the state of the art. It is, however, also very advantageously applicable for use alone on its own merits or in combination with a conventional measuring half-cell.

The invention relates also to a measuring arrangement comprising a process container with a container wall and a potentiometric sensor apparatus according to one of the above described embodiments, wherein the sensor apparatus is connected with the container wall in such a manner that at least the immersion region of the sensor apparatus is accessible from the interior of the process container. The container can be a process container, especially a fermenter, a reactor, a pipeline or some other container containing or conveying process medium. Especially, the container can be a single-use container, for example, one with a flexible wall.

For performing a two- or multipoint calibration, the measuring arrangement can have at least a second coating applied on a surface arranged within the process container and including a second calibration means, wherein the sensor apparatus is movable relative to the second coating applied on the surface arranged within the process container from a starting position, in which the measuring membrane of the sensor apparatus does not contact the second coating, into an end position, in which the measuring membrane of the sensor apparatus does contact the second coating for performing a calibration by means of the second calibration means. The surface arranged within the process container can be, for example, an inner surface of a housing wall of the process container.

For a multipoint calibration, other surface regions within the process container can comprise coated regions, wherein each coated region includes a calibration means.

A two point calibration can be performed in that, directly after introducing a liquid into the process container, the first coating and the second coating present on the measuring membrane, which can be arranged e.g. on the inner surface of the process container, begin to gel by absorbing liquid, especially water, and so form a gel comprising the calibration means or a viscous polymer electrolyte comprising the calibration means. The liquid introduced into the process container can be, for example, water, a cleaning liquid or a process medium, e.g. a nutrient solution for a biochemical, or biotechnological process. First, a first calibration measurement is performed by means of the first calibration means contained in the coating arranged on the measuring membrane. If the sensor apparatus is a potentiometric pH-sensor, the first calibration means can be a pH-buffer, especially one of the buffer systems mentioned above. After the dissolving of the first coating in the liquid, the sensor apparatus including the measuring membrane can be moved into the end position, so that the measuring membrane contacts the second coating with the second calibration means for performing a second calibration measurement. If the sensor apparatus is a pH-sensor, the second calibration means can, in turn, be a pH buffer, whose pH-value is different from that of the first calibration means. Preferably, also the second coating gels in contact with the liquid for forming a gel or polymer electrolyte containing the second calibration means, but dissolves, however, more slowly in the liquid than the first coating, so that, after the dissolving of the first coating, there is still a sufficient amount of second calibration means available for performing the second calibration measurement. This can be achieved, for example, by having the first coating, as basic material, be a short chained oligomer, or polymer or a polymer with a lesser degree of crosslinking than the second coating.

In an alternative embodiment, the second or a number of other coatings comprising calibration means can be arranged on a surface of a movable component, e.g. on a revolving wheel, movable relative to the measuring membrane. By rotating the revolving wheel, the membrane can be brought in contact one after the other with the thereon applied coatings for one or more other calibration measurements.

BRIEF DESCRIPTION OF THE DRAWINGS

The invention will now be explained in greater detail based on the examples of embodiments illustrated in the drawing, the figures of which show as follows:

FIG. 1 is a schematic representation of a first pH-sensor apparatus suitable for dry storage over a longer period of time;

FIGS. 2a) and 2b) are a schematic representation of a first measuring arrangement with a potentiometric sensor apparatus, which is affixed in a wall of a process container, and which furthermore includes means for performing a two point calibration;

FIGS. 3a) and 3b) are a schematic representation of a second measuring arrangement with a potentiometric sensor apparatus, which is affixed in a wall of a process container, and which includes means for performing a two point calibration;

FIGS. 5a) and 5b) are a schematic representation of a first potentiometric sensor apparatus, which is embodied upon start-up to transport liquid into its reference half-cell chamber via a dialysis membrane;

FIGS. 6a) and 6b) are a schematic representation of a second potentiometric sensor apparatus, which is embodied upon start-up to transport liquid into its reference half-cell chamber via a dialysis membrane;

FIG. 8 is a second graph illustrating the different drift behavior of potentiometric sensors with and without coating of the measuring membrane after a longer dry storage phase.

DETAILED DISCUSSION IN CONJUNCTION WITH THE DRAWINGS

Figure 4:
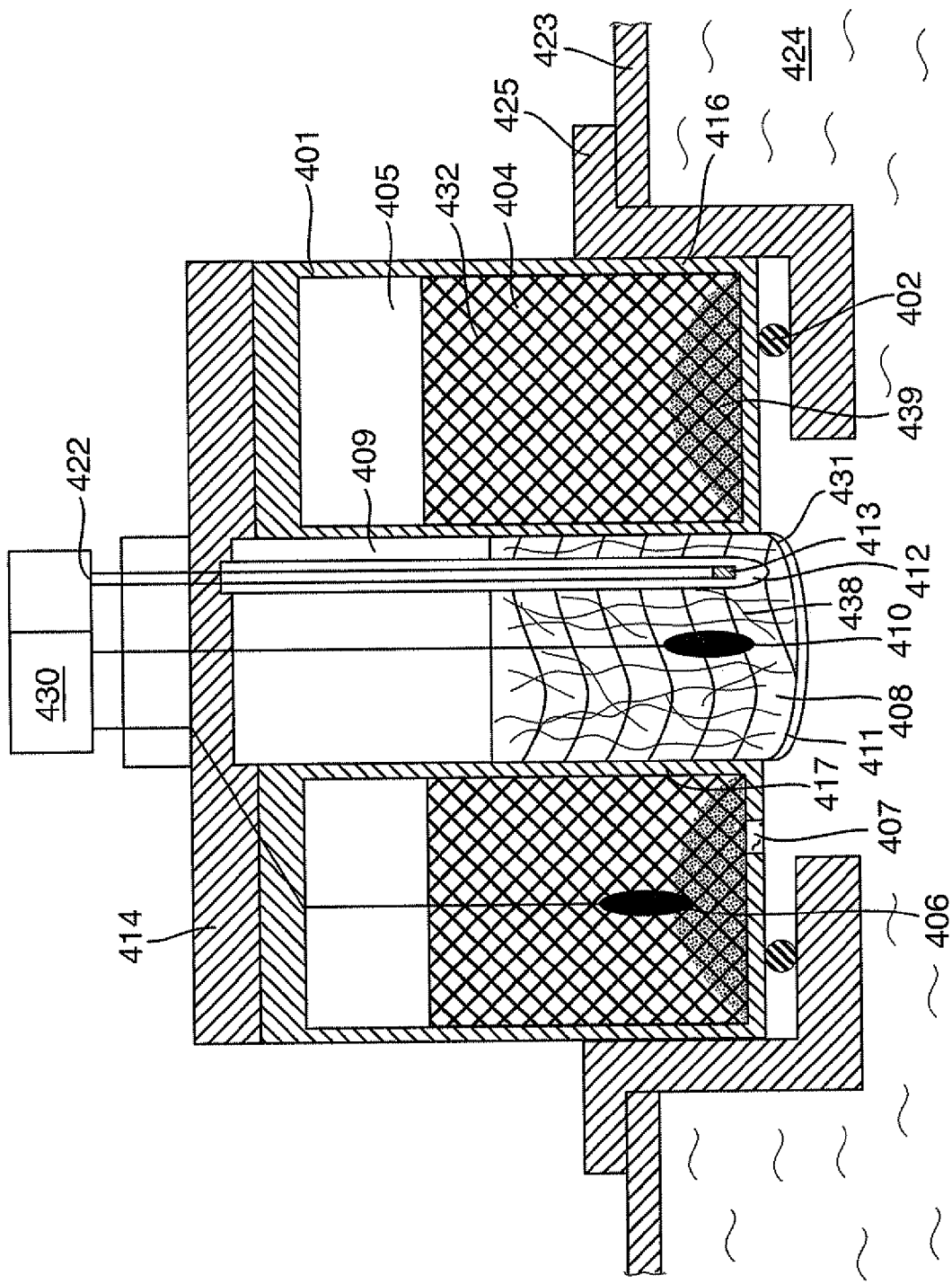
FIG. 4 is a schematic representation of a second pH-sensor apparatus suitable for dry storage over a longer period of time.

FIG. 1 shows a potentiometric sensor apparatus for pH measurement with a housing 1 of an insulating material. The sensor apparatus includes a reference half-cell chamber 5, in the form of an annular chamber, and an essentially cylindrical measuring half-cell chamber 9 surrounded by the annular chamber. The insulating material can be glass or a polymer material, such as, for example, polyetheretherketone (PEEK).

The reference half-cell chamber 5 is surrounded by an outer tubular housing wall 16 and a thereto concentrically arranged, inner tubular housing wall 17, as well as by two annular housing walls lying opposite one another and extending perpendicularly to the shared cylindrical symmetry axis of the tubular housing walls 16, 17 and connecting these with one another. The measuring half-cell chamber 9 is surrounded by the inner tubular housing wall 17, which is closed on its one end by the measuring membrane 11 and on its other end by a housing wall 14 lying opposite the measuring membrane 11.

Housing 1 of the potentiometric sensor apparatus is accommodated in a holder 25, which is connected fixedly, for example, by adhesion or welding, with a single use, process container 23. Housing 1 can be pressed in the holder, for example, by means of a screwed connection, against the sealing ring 2, so that liquid 24 contained in the process container 23 cannot leak from the interior of the process container 23 into the environment 26. The region surrounded by the sealing ring 2 is the immersion region of the potentiometric sensor apparatus I coming in contact with the liquid 24.

In the present example, measuring membrane 11 is a pH-selective, glass membrane. Preferably, the glass membrane comprises a low-ohm glass, what provides a rapid response, even in the case of small glass membrane areas, especially also upon start-up of the sensor. The glass membrane 11 can be welded onto a glass tube, which is pressed into the inner tubular housing wall 17 comprising the measuring half-cell chamber 9 or adhered with the inner side of the housing wall 17. The glass tube is closed on its end lying opposite the measuring membrane 11 by the housing wall 14; it can also be melted or adhered closed on such end, or closed by a sealing element, such as e.g. a plug of a polymer material. If the potentiometric sensor is embodied in the form of an ion-selective electrode for determining an ion concentration, the measuring membrane 11 can comprise a polymer membrane with or without softeners, plasticizers, conductive salts and/or ionophores.

Measuring membrane 11 includes a coating 31, which comprises a polymer material gelling in contact with a water containing liquid. Thus, the polymer material can be, especially, a water soluble, polymer material, and can contain a dry or low moisture, buffer system embedded in the polymer material. Upon contact of the coating with a water containing liquid, the polymer material gels, i.e. water from the liquid penetrates into the polymer material and forms with the buffer system embedded in the polymer material a buffer solution, which can serve for calibration of the sensor apparatus.

Coating 31 can be formed, for example, by one or more immersion coatings (dip coatings) of the measuring membrane 11 in a buffer solution containing a water soluble polymer. Coating 31 can be, for example, PEG with an acetic acid/acetate buffer system embedded therein.

The measuring half-cell chamber 9 contains an inner electrolyte 8, into which a potential sensing element 10 extends. The inner electrolyte 8 can be embodied as a firm electrolyte gel comprising a buffer system or it can be a water containing buffer solution. The non-electrolyte filled compensation space of the measuring half-cell 9 can contain air or a polymer compensator, e.g. silicone foam.

In the example shown here, measuring half-cell chamber 9 contains an assembly of fibers 32 of a hydrophilic material, for example, of glass containing aluminum oxide- and/or silicon oxide. The fiber separations are so selected that the inner electrolyte 8 is transported by means of capillary forces even counter to the force of gravity toward the measuring membrane 11, in order to assure a wetting of the inner side of the measuring membrane 11 by the inner electrolyte independently of the spatial orientation of the measuring half-cell. This permits stable operation of the sensor apparatus in any imaginable, installed position.

Accommodated in the reference half-cell chamber 5 is a reference electrolyte 4, into which a potential sensing element 6 extends. The reference electrolyte 4 can be, for example, a firm electrolyte gel, which contains a water containing 3 M potassium chloride solution, or a liquid electrolyte, e.g. a water containing 3 M potassium chloride solution. The potential sensing element 6 is, for example, a chloridized silver wire. The remaining, space of the first chamber 5 not filled by the reference electrolyte 4, also referred to as compensation space, can contain air or also a polymer compensator, e.g. silicone foam.

In the annular housing wall bounding the reference half-cell chamber 5 on its measuring membrane side is arranged, serving as liquid junction, a diaphragm 7, via which the reference half-cell is in communication with the environment of the housing 1 for the exchange of charge carriers. In measurement operation of the sensor apparatus, diaphragm 7 provides an electrical, ionically conductive connection between the reference electrolyte 4 and the liquid 24 present outside the reference half-cell. The liquid junction can alternatively also be embodied as one or more bores in the housing wall or as an annular gap surrounding the measuring membrane 11. In the example shown here, diaphragm 7 is embodied as a pin of a microporous ceramic, for example, a micropored, zirconium dioxide ceramic.

Supplementally arranged in the measuring half-cell chamber 9 in the example shown in FIG. 1 is a temperature sensor 13, which comprises a temperature dependent resistor arranged in a capillary 12 of glass or synthetic material and so electrically insulated from the inner electrolyte 8. Temperature sensor 13 is only optionally present and can serve in the case of determining the pH-value from the potential difference ascertained by the measurement circuit 30 between measuring half-cell and reference half-cell to take the temperature dependence of the pH-value into consideration.

Electrical lines for contacting the potential sensing element 10 of the measuring half-cell, the potential sensing element 6 of the reference half-cell and the temperature sensor 13 are led through the housing wall 14, which can also be embodied as potting compound, to a plug, which has pins 22, a plug, which, in given cases, is at least partially incorporated in the potting compound. Pins 22 serve as contact locations of the potential sensing elements 6, 10 and of the temperature sensor arranged outside of the housing 1. Pins 22 can be connected electrically conductively with a measurement circuit 30 or directly with a measurement transmitter for forming a complete measuring device.

The potential difference between the reference half-cell and the measuring half-cell tappable between the sensing elements 6, 10 depends on the pH-value of the medium contacting the measuring membrane 11. So long as a sufficiently thick coating 31 of a gel-, or polymer electrolyte containing a buffer system covers the measuring membrane 11, the potential difference is essentially determined by the pH-value of the buffer system. When the coating 31 has dissolved in the liquid 24, which can be, for example, a process medium of a biological, biochemical or biotechnological process to be monitored by the sensor apparatus, the potential difference is then determined essentially by the pH-value of the liquid 24. The potential difference is registered as measurement signal by a measurement circuit 30 connected with the two sensing elements 6, 10, digitized and by means of a data processing unit of the measuring device, for example, in a measurement transmitter, mapped to a measured value based on a characteristic curve furnished in a memory of the measurement transmitter. The measurement transmitter includes for this purpose a corresponding computer program, which can be executed by the data processing unit. In the case of pH measurement, the registered potential difference between reference- and measuring half-cell is mapped to a pH-value. Used as characteristic curve in the case of a potentiometric pH-sensor is, as a rule, a straight line, which is defined by a zero-point, or abscissa intersection, and a slope. By means of calibration measurements, zero-point and slope can be determined in manner known per se and, in given cases, an adjusting of the measuring device can be performed.

The coating 31 of the measuring membrane 11 effects an accelerated response for the measured value of the sensor apparatus after a longer time span of dry storage and/or after a sterilization by means of gamma radiation, in comparison to an equally-constructed sensor apparatus without the coating 31. The terminology 'response of a sensor apparatus' means that time span, within which the measurement circuit of the sensor apparatus, after start-up by immersion of the immersion region of the sensor apparatus in a liquid, for example, a buffer solution with constant pH-value, outputs a measured value, which fluctuates, if at all, only within a predetermined tolerance range.

Experiments described in the following show, by way of example, the acceleration of the response using a coating of the measuring membrane. Used for the experiments were sensors having a measuring membrane 11 of a first pH-sensitive glass and sensors with a measuring membrane 11 of a second pH-sensitive glass different from the first pH-sensitive glass.

In a first experiment, all sensors were first dried (2 hours at 80° C.). A sensor with a measuring membrane 11 of the first pH-sensitive glass (sensor 6) and a sensor with a measuring membrane of the second pH-sensitive glass (sensor 7) were immersion coated in a 1% hydroxy ethyl cellulose solution. Both sensors as well as two uncoated comparison sensors of the first pH-sensitive glass (sensors 1 and 2) were stored dry over a time period of, for example, 1 week.

Figure 7:
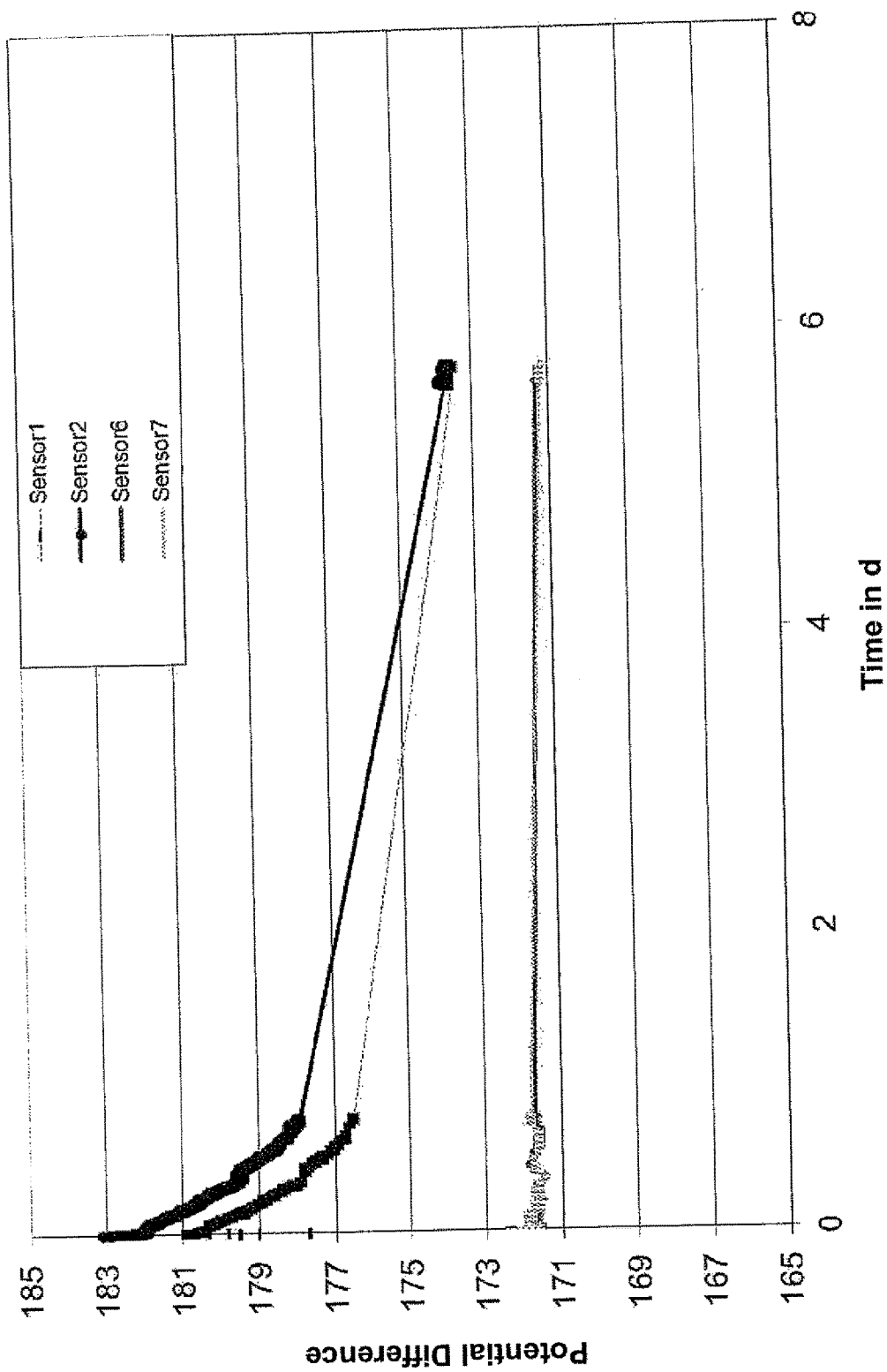
FIG. 7 is a first graph illustrating the different drift behavior of potentiometric sensors with and without coating of the measuring membrane after a longer dry storage phase.

FIG. 7 shows the drift behavior of the measurement signals obtained with the four sensors after start-up in a buffer solution of pH=4. Plotted on the ordinate is the value of the measurement signal, thus the potential difference in mV registered between reference- and measuring half-cells, and on the abscissa the time in days (d). It is clear that the coated sensors 6 and 7 deliver from the beginning a more stable measurement signal than the uncoated sensors, whose measurement signals lay only after, for instance, the third day constantly within a tolerable tolerance range.

A second experiment was performed as in the case of the first experiment, wherein the sensors 6 and 7 were immersion coated doubly by immersion into the 1% hydroxy ethyl cellulose solution. FIG. 8 shows the drift behavior of the two doubly coated sensors 6 and 7 as well as the uncoated comparison sensors 1 and 2 upon start-up in a buffer solution with pH=4 after one week of dry storage. As in FIG. 7, plotted also here on the ordinate is the value of the measurement signal in my and on the abscissa the time in days (d). Again, it is evident that the coated sensors 6 and 7 deliver from the beginning a relatively stable measurement signal, which already after two days lay within an acceptable tolerance range of +/−2 mV, while the measurement signal of the uncoated sensors 1 and 2 achieved this state only after 4 days.

The fluctuations of the measurement signal seen in FIG. 8 extending equally for all sensors result essentially from time of day dependent, temperature fluctuations.

If the coating 31 contains supplementally a calibration means, e.g. a buffer system, which, upon taking up liquid as the coating gels, forms a calibration solution bound into the coating 31, e.g. in the case of a pH-sensor apparatus a buffer solution with a stable pH-value, a calibration measurement can be performed in the time span between the forming of the buffer solution as the coating gels and the dissolving of the coating 31 off of the measuring membrane. The basic performability was demonstrated in experiments described as follows.

EXAMPLE 1 a) Coating the Measuring Membrane

For coating a conventional pH-sensitive, glass membrane of a pH-sensor apparatus, produced as immersion solution was a water containing solution set at pH=4 with a conventional buffer system (citric acid, hydrochloric acid) and having a PEG-content of 50 wt.-%. The measuring membrane of the sensor apparatus was immersion coated by multiple immersions of the membrane. Each immersion was followed by a drying.

b) First Measurement: Start-Up of the Sensor Apparatus After Dry Storage

The sensor apparatus was stored dry over a period of 7 days. Then, it was immersed in deionized water. Thereafter, the sensor apparatus was immersed in a first buffer solution of pH=7 and a second buffer solution of pH=9.18 and measured values registered (results are presented in Table 1).

c) Second Measurement: Start-Up of the Sensor Apparatus After Dry Storage and Sterilizing with a Dosage of 25 kGy The sensor apparatus was stored dry over a period of 7 days and then irradiated with gamma radiation with a dosage of 25 kGy. Start-up occurred in equal manner as described under b) by immersion of the sensor apparatus sequentially in deionized water, a first buffer solution of pH=7 and a second buffer solution of pH=9.18, wherein, in each liquid, measured values were registered (measurement results are presented in Table d) Third Measurement: Start-Up of the Sensor Apparatus After Dry Storage and Sterilizing with a Dosage of 2 Times 25 kGy The sensor apparatus was stored dry over a period of 7 days and then doubly irradiated with gamma radiation of, in each case, a dosage of 25 kGy. Then, start-up occurred in equal manner as described under b) and c), wherein, upon immersion in each liquid, measured values were registered (measurement results are presented in Table 1).

e) Observation:

In the case of each of the measurements b)-d), already after 2 seconds, a stable measurement signal at pH-value 4 corresponding to around 165 mV could be observed. After an additional 30 seconds there began a shifting of the measurement signal to lower potentials. This can be explained by the dissolving of the coating off of the measuring membrane. The measurement signals registered subsequently in the buffer solutions lie in the normal range. The measurement results are given in Table 1.

TABLE 1

|  | pH4 | pH7 | pH9.18 | Slope | |
|---|---|---|---|---|---|
| Measure b) | 165 | −8 | −127 | 173 | 98.5% |
| Measure c) | 163 | −11 | −137 | 174 | 99.0% |
| Measure d) | 164 | −10 | −133 | 174 | 99.0% |

EXAMPLE 2

For coating a conventional pH-sensitive, glass membrane of a pH-sensor apparatus, produced as immersion solution was a water containing solution set at pH=4 with a conventional buffer system (citric acid, HCl) and having a hydroxy ethyl cellulose (HEC) content of 2 wt.-%. The measuring membrane of the sensor apparatus was immersion coated by multiple immersions of the membrane. Each immersion was followed by a drying.

Measurements were performed on the coated sensor apparatus as described under b) to d) in Example 1.

Upon start-up of the sensor apparatus, a stable measurement signal of about 164 mV was observed already after 2 seconds. Then, after 15 minutes, there occurred the shifting of the measurement signal into the basic region. The measurement results are combined in Table 2.

TABLE 2

|  | pH4 | pH7 | pH9.18 | Slope | |
|---|---|---|---|---|---|
| Measure b) | 164 | −10 | −129 | 174 | 99.0% |
| Measure c) | 161 | −11 | −137 | 172 | 97.9% |
| Measure d) | 164 | −9 | −133 | 173 | 98.5% |

The application of a polymer coating comprising a buffer system with a measuring membrane coating gelling in the presence of water permits, thus, a one point calibration of the sensor apparatus.

FIGS. 2a and b show, schematically, an arrangement for performing a two point calibration of a sensor apparatus 100. The sensor apparatus 100 can be embodied, for example, as the sensor apparatus 1 shown in FIG. 1. Housing 101 of the sensor apparatus 100 is integrated by means of a holder 125 into a container wall of a process container 123 and sealed by means of the seal 102 relative to the interior of the process container 123. The process container 123 can be, for example, a pipeline with solid or flexible wall. Holder 125 includes a flexible membrane 129, which enables an axial movement of the sensor apparatus 100 within the holder 125.

The measuring membrane 111 is, as described at length based on the sensor apparatus illustrated in FIG. 1, provided with a coating 131, which includes a first calibration means, e.g. a buffer system. Applied on the wall of the process container 123 lying opposite the measuring membrane 111 is a second coating 135, which includes a second calibration means, e.g. a second buffer system. The second coating 135 includes, same as the coating 131 of the measuring membrane, a component, e.g. a water soluble polymer, gelling in contact with a water containing liquid and the respective buffer system is embedded in such component. If a process liquid 124 is flowing through the process container 123, the two coatings 131, 135 gel and form a pH-buffered polymer electrolyte or a pH-buffered electrolyte gel. In such case, the first and the second buffer systems are so selected that the polymer electrolytes, or electrolyte gels, formed by the gelling of the coatings 131 and 135 have different pH-values. The polymer material of the coatings can be so selected that the coating 131 of the measuring membrane 111 dissolves faster in the process liquid 124 than the second coating 135.

Housing 101 is axially movable between a first position (FIG. 2a), in which the measuring membrane 111 is spaced from the oppositely lying container wall of the process container 123, and a second position (FIG. 2b), in which the measuring membrane 111 contacts the second coating 135 arranged on the oppositely lying container wall of the process container 123. The axial movement of the housing 101 toward the process container 123 into the second position compresses a spring 136 against the housing wall, so that the return force of the spring 136 effects an axial movement of the housing 101 back into the first position.

Upon start-up of the sensor apparatus, liquid 124, e.g. deionized water or a water containing process medium of the process performed in the process container 123, is introduced into the process container 123, so that the coatings 131 and 135 begin to gel and pH-buffered, polymer electrolytes form. In the first position (FIG. 2a)), there occurs then a first calibration measurement. After the dissolving of the coating 131 in the liquid 124, which is indicated by a change of the measurement signal of the sensor apparatus earlier constant over a certain time period (compare above Example 1), the housing is moved axially into the second position (FIG. 2b)). In this position, the measuring membrane 111 contacts the pH-buffered gel electrolyte formed by the gelling of the second coating 135, so that a second calibration measurement can be performed at the pH-value of this electrolyte. After termination of the calibration measurement, the sensor apparatus is shifted back into the first position and normal measurement operation is begun.

Another arrangement for performing a two point calibration is shown schematically in FIGS. 3a and b. In this arrangement, the housing 201 of the sensor apparatus 200, which, in turn, can be embodied as the sensor apparatus based described on FIG. 1, is integrated in a holder 225 in a wall of a process container 223. Process container 223 includes in this example of an embodiment a flexible container wall. As in the case of the example of an embodiment described based on FIGS. 2a and b, a first coating 231 with a first buffer system is applied on the measuring membrane 211 of the sensor apparatus 200, while a second coating 235 with a second buffer system is arranged on the wall of the process container 223 lying opposite the measuring membrane 211.

If liquid 224 is led through the process container 223, the two coatings 231, 235 gel and form, in each case, a pH-buffered, gel electrolyte, wherein the buffer systems are so selected that the two gel electrolytes have different pH-values. The first calibration measurement is performed, so long as the first coating 231 has still not dissolved off of the measuring membrane 211. After the dissolution of the first coating 231, the flexible wall can be deformed in such a manner that the coating 235 comes in contact with the measuring membrane 211, in order to perform a second calibration measurement (FIG. 3b). After terminating the calibration measurement, the container wall is brought back into its original position (FIG. 3a) and normal measurement operation begun.

FIG. 4 shows, schematically, a second pH-sensor apparatus suitable for dry storage over a longer period of time. The embodiment of the sensor housing, the potential sensing elements and the measurement circuit as well as the measuring half-cell is essentially the same as in the case of the sensor apparatus described based on FIG. 1. The sensor apparatus is secured by means of a holder 425 in the wall of a process container 423, in which a liquid 424 is contained. A sealing between the housing 401 of the sensor apparatus and the process container 423 is achieved by means of a seal 402.

The sensor apparatus shown in FIG. 4 includes, same as the sensor apparatus described based on FIG. 1, a measuring half-cell having a pH-sensitive measuring membrane 411, an inner electrolyte 408 accommodated in a measuring half-cell chamber 409 and a potential sensing element 410 protruding therein. The measuring membrane 411 is covered by a coating 431, which, as described at length above based on FIG. 1, is embodied to accelerate the response of the sensor apparatus after dry storage. Contained in the measuring half-cell chamber 409 is, moreover, a temperature sensor 413 embedded in a capillary 412 of glass or synthetic material. Contained within the measuring half-cell chamber 409 is an assembly of glass fibers 438, wherein the glass contains aluminum oxide or silicon oxide.

The sensor apparatus includes, surrounding the measuring half-cell chamber 409, a ring-shaped, reference half-cell chamber 405, into which a potential sensing element 406 protrudes. The potential sensing element 406 of the reference half-cell and the potential sensing element 410 of the measuring half-cell are connected via a connection plug 422 with a measurement circuit 430, which is embodied to register a potential difference between the sensing elements 406, 410 and to output such as measurement signal, in given cases, amplified and/or digitized. In the present example, the measurement circuit 430 registers also a signal from the temperature sensor 413. This can be registered and processed by a superordinated data processing system, for example, a measurement transmitter, connected with the measurement circuit, in order to take into consideration the temperature dependence of the pH-value.

Arranged in the reference half-cell chamber 405 is a fibrous weave 432 of glass fibers as well as dry potassium chloride-salt in the form of a heap 439. Arranged within the immersion region of the sensor apparatus bounded by the seal 402 is a liquid junction 407 embodied as a passageway. The fibrous weave 432 is embodied, to transport, by capillary action, liquid 424 through the liquid junction 407 into the reference half-cell chamber 405. The potassium chloride salt contained in the reference half-cell chamber dissolves in the liquid transported into the reference half-cell chamber 405 to form a liquid reference electrolyte.

This sensor apparatus can, either isolated from the process container 423 or, as shown in FIG. 4, integrated into the process container 423, be stored dry over a longer period of time of some days out to some months and/or be sterilized by means of a high dosage of gamma radiation. For example, an option is to sterilize the process container 423 and the therein integrated sensor apparatus together and then to store the integrated pair a longer period of time. If the process container 423 is then to be used in a biotechnological process, in a first step, a liquid 424, for example, deionized water or a process medium of the process, can be led into the process container. As soon as the immersion region of the sensor apparatus bounded by the seal 402 comes in contact with the liquid 424, on the one hand, the coating 431 begins to gel in the above described manner, while, on the other hand, liquid 424 is transported through the liquid junction 407 into the reference half-cell chamber 405, in order to form a reference electrolyte. Within a short time, i.e. within a few minutes in the case of a reference half-cell chamber volume of 0.1 to 10 ml, in this way, a stable measurement signal of the sensor apparatus is achieved.

Instead of the fibrous weaves 432, also a glass fiber assembly, hoses, tubes, sponges or filaments of inorganic fiber material can be used. Preferably involved are inorganic materials such as aluminum oxide, titanium oxide or silicon oxide with very finely twisted capillaries with a fiber separation of less than 100 µm. The fibers can be formed of twisted filaments, wherein the capillary action is controlled by the amount of twisting and therewith by the mutual separations of the filaments from one another. In an example of an embodiment, the glass fiber filaments can be twisted in a slightly wetted state and inserted into a glass tube, which then is installed into the wall of the sensor housing as the liquid junction. In given cases, the fiber can be treated with a small amount of siloxane, so that the filaments are held together in the manner of a wick, even without an outer wall.

For lessening the out flow of reference electrolyte from the reference half-cell chamber 5, an inorganic thickening means, such as silicon oxide, titanium oxide or aluminum oxide in powder form, can be present in the reference half-cell chamber 405. These materials form, in contact with aqueous liquid, linear, laminar or spherical colloids and so bring about a gradual thickening of the reference electrolyte, first of all, liquid, composed of the potassium chloride salt and the liquid transported through the liquid junction. Likewise suitable for thickening the reference electrolyte are additives of reactive components, as cement or esterified siloxanes, e.g. tetraethyl orthosilicate (TEOS). As advantageous has been found the mixing in of these agents in encapsulated form, for example, encapsulated in silicon oxide, titanium oxide, aluminum oxide or organic filler bodies such as poly(meth)acrylic acid ester, poly(meth) acrylic acid or poly(methacrylic acid ethylene phosphate). The thickening of the reference electrolyte by one or more of these additives has the additional advantage that the sensor apparatus can be applied in any imaginable orientation.

In the case of both examples of embodiments of sensor apparatuses described here (FIG. 1 and FIG. 4), antioxidants can be present in the reference- and/or measuring half-cell chamber, in each case, as other additives for improving the storability, or sterilization resistance, of the sensor apparatuses.

In an alternative embodiment, the transport of liquid into a reference half-cell chamber embodied first for dry or low moisture storage can occur through a dialysis membrane. This is illustrated in FIG. 5 and FIG. 6. FIG. 5*a* shows, schematically, a section of the immersion region side of a sensor apparatus 500 integrated into the wall of a process container 523, as such was already described based on FIG. 1 or FIG. 4. Sensor apparatus 500 includes a measuring half-cell with a pH-sensitive measuring membrane 511 and a reference half-cell with a reference half-cell chamber 505, which are, in each case, indicated in FIG. 5 only schematically. The reference half-cell includes as liquid junction a dialysis membrane 540, whose pore size is so selected that it only is porous for water molecules and ions, however, not for larger molecules, such as e.g. glucose.

Potassium chloride can be present within the reference half-cell chamber 505 dissolved or suspended in a low moisture solvent, e.g. low moisture (98%) glycerine solution. In this embodiment, water is transported from the liquid 524 within the process container 523 through the dialysis membrane 540 into the reference half-cell chamber 505. As soon as a sufficient amount of water has been transported through the membrane 550 into the reference half-cell chamber 505, so that the reference electrolyte formed, in this way, in the reference half-cell chamber 505 has a concentration of about 3 mol/l KCl, a stable measurement signal is obtain from the sensor apparatus. The membrane 550, which is also transmissive for ions, in this embodiment simultaneously forms the liquid junction of the reference half-cell.

Another variant is shown schematically in FIG. 6. FIG. 6*a* shows a section on the immersion region side of a sensor apparatus 600 arranged in a wall of a process container 623 and embodied, for example, in the manner of the sensor apparatus described based on FIG. 1 or FIG. 4. Sensor apparatus 600 includes a measuring half-cell with a pH-sensitive measuring membrane 611 and a reference half-cell with a reference half-cell chamber 605, which, in each case, are indicated only schematically in FIG. 6. The reference half-cell includes as liquid junction 607 a bore elongated axially into in the reference half-cell chamber 605 by an attached small tube 641, for example, of glass or a polymer material. The reference half-cell chamber 605 is sealed from the process container 623 by a dialysis membrane 650 arranged in the immersion region. Contained within the reference half-cell chamber 605 is KCl dissolved or suspended in a low moisture solvent, for example, in a low moisture glycerine solution. Water is transported through the dialysis membrane 650 from the process container 623 into the reference half-cell chamber 405, in order to form a reference electrolyte solution therein. When the liquid level reaches the height of the end of the small tube 641 facing away from the process, an electrolytic contact forms between the reference electrolyte and the liquid 624 contained in the container 623 (FIG. 6*b*)). From this point in time onwards, measurements can be performed with the sensor apparatus 500.

The invention claimed is:

1. A potentiometric sensor apparatus, comprising:
   a measuring half-cell including a measuring membrane comprising glass, the measuring membrane having a gel layer covered by a coating during dry storage of the potentiometric sensor apparatus, wherein the coating maintains the gel layer, keeping the gel layer functional during dry storage of the sensor apparatus;
   at least one immersion region, which includes the measuring membrane and the coating;

a reference half-cell; and
a measurement circuit for registering a potential difference between said measuring half-cell and said reference half-cell,
wherein the coating is embodied such that, in operation, upon immersion of at least a portion of the immersion region in a water-containing liquid and upon continued contact with the water-containing liquid, the coating at least partially dissolves from the measuring membrane,
wherein the coating includes a substance that, in operation, gels in contact with the water-containing liquid and is soluble or dissolves in the water, including one or more substances of the group consisting of urea or polyurea, polyethylene imine, poly(methacrylic acid), cellulose, polyvinyl alcohol and derivatives thereof, and
wherein the coating includes a calibration means for performing a calibration of the potentiometric sensor apparatus.

2. The potentiometric sensor apparatus as claimed in claim 1, wherein after dry storage and/or a sterilization of the potentiometric sensor apparatus with gamma radiation of a total radiation dosage of at least 25 kGy over a predetermined first time span, a second time span from the immersion of the immersion region of the potentiometric sensor apparatus into the liquid to the reaching of a potential difference, constant within a predetermined tolerance range, between said measuring half-cell and said reference half-cell is shorter than a second time span for a potentiometric sensor apparatus without the coating from the immersion of the immersion region into the liquid to the reaching of a potential difference, constant within the predetermined tolerance range, between said measuring half-cell and said reference half-cell after dry storage and/or a sterilization with gamma radiation of a total radiation dosage of at least 25 kGy during the predetermined first time span.

3. The potentiometric sensor apparatus as claimed in claim 1, wherein the coating has no toxic and/or cytotoxic properties.

4. The potentiometric sensor apparatus as claimed in claim 1, wherein the gel layer comprises a plurality of hydroxyl groups, and wherein the coating is embodied to stabilize at least one part of the hydroxyl groups and/or to exchange protons with said measuring membrane for forming hydroxyl groups.

5. The potentiometric sensor apparatus as claimed in claim 1, wherein the calibration means includes a calibration pH buffer system, the pH buffer system including at least one water soluble oligomer or polymer component, including an oligomer or polymer component, which has at least one acid group, including a carbonyl acid, phosphoric acid, phosphonic acid or a sulfonic acid group.

6. The potentiometric sensor apparatus as claimed in claim 5, wherein the polymer component is selected from the group consisting of methacrylates and their copolymers or polymers with organic phosphate groups, including ethylene glycol (meth)acrylate phosphate, monostarch phosphate, distarch phosphate, phosphated distarch phosphate, acetylated distarch phosphate, poly(acrylphosphonic acid), Nafion and derivatives thereof.

7. The potentiometric sensor apparatus as claimed in claim 1, wherein the coating includes at least one antioxidant, including a radical interceptor, including an antioxidant selected from the group consisting of silver salts, 2,2,6,6-tetramethyl piperidinyl oxyl (TEMPO), phosphate- or carbonate buffer, rosmarinic acid, citric acid and ascorbic acid.

8. The potentiometric sensor apparatus as claimed in claim 1, wherein said measuring half-cell has a measuring half-cell chamber formed in a housing of the potentiometric sensor apparatus, sealed by the measuring membrane, and containing an inner electrolyte, which has a water content of less than 60%.

9. The potentiometric sensor apparatus as claimed in claim 8, wherein said measuring half-cell chamber contains a porous body and/or fibers, including a fibrous weave or an assembly of fibers having a fiber separation of less than 100 micrometers, and/or at least one capillary tube, and/or a powder.

10. The potentiometric sensor apparatus as claimed in claim 9, wherein said porous body, the fibers, the capillary tubes and/or the powder comprise(s) a hydrophilic material, including aluminum oxide, titanium oxide and/or silicon oxide or a glass containing aluminum oxide, titanium oxide and/or silicon oxide.

11. The potentiometric sensor apparatus as claimed in claim 1, wherein:
said reference half-cell includes a reference half-cell chamber defined by a housing of the potentiometric sensor apparatus and a liquid junction arranged in a wall of said housing within the immersion region of the sensor apparatus;
a dry or low moisture substance is contained in said reference half-cell chamber; and
said reference half-cell is embodied to enable transport of liquid through the liquid junction into said reference half-cell chamber to form a reference electrolyte with the substance contained in said reference half-cell chamber.

12. The potentiometric sensor apparatus, as claimed in claim 1, wherein:
the reference half-cell includes a reference half-cell chamber formed in a housing of the potentiometric sensor apparatus, and a liquid junction arranged in a wall of said housing within an immersion region of the potentiometric sensor apparatus intended for immersion of the sensor apparatus in a measured medium;
a substance is contained in said reference half-cell chamber; and
said reference half-cell is embodied to transport liquid through the liquid junction into the reference half-cell chamber to form a reference electrolyte from the substance contained in said reference half-cell chamber and the liquid transported into said reference half-cell chamber.

13. The potentiometric sensor apparatus as claimed in claim 11, wherein said reference half-cell has transport means for the transport of liquid through the liquid junction into said reference half-cell chamber, and said transport means thereto are embodied to transport the liquid by means of capillary forces.

14. The potentiometric sensor apparatus as claimed in claim 13, wherein said transport means comprises a porous body and/or fibers, including a fibrous weave or an assembly of fibers with a fiber separation of less than 100 micrometers, and/or a dialysis membrane, and/or at least one capillary tube and/or a powder.

15. The potentiometric sensor apparatus as claimed in claim 14, wherein said porous body, the fibers, the capillary tubes and/or the powder comprise a hydrophilic material, including a glass or a ceramic, containing aluminum oxide and/or titanium oxide and/or silicon oxide.

16. The potentiometric sensor apparatus as claimed in claim 14, wherein the dialysis membrane is a material having an average exclusion volume of less than 50 kDa, including a polymer material selected from the group consisting of acetylated cellulose derivatives, including cellulose esters, ethyl cellulose, alkylene oxide/alkyl glycidyl ether-copolymers, polyglycols, polymeric epoxides, poly (lactic acid) derivatives, and water insoluble acrylates, including copolymers based on ethyl acrylate and/or methyl methacrylate.

17. The potentiometric sensor apparatus as claimed in claim 11, wherein the liquid junction is embodied as an annular gap, a pore or a membrane.

18. A measuring arrangement comprising:
  a process container with a container wall and a potentiometric sensor apparatus, the potentiometric sensor apparatus comprising:
    a measuring half-cell including a measuring membrane composed of glass, the measuring membrane having a leaching layer covered by a coating during dry storage of the potentiometric sensor apparatus;
    at least one immersion region, which includes the measuring membrane;
    a reference half-cell; and
    a measurement circuit for registering a potential difference between said measuring half-cell and said reference half-cell,
  wherein the coating is embodied to maintain leaching layer, keeping the leaching layer functional during dry storage of the sensor apparatus, and further embodied such that, in operation, upon immersion of at least a portion of the immersion region of the potentiometric sensor apparatus in a water-containing liquid, and upon continued contact with the water-containing liquid, the coating at least partially dissolves from the measuring membrane,
  wherein the coating includes a substance that, in operation, gels in contact with the water-containing liquid and is soluble or dissolves in the water, including one or more substances of the group consisting of urea or polyurea, polyethylene imine, poly(methacrylic acid), cellulose, polyvinyl alcohol and derivatives thereof,
  wherein the potentiometric sensor apparatus is connected with the container wall such that at least the immersion region of the sensor apparatus is accessible from the interior of the process container, and
  wherein the coating includes a calibration means for performing a calibration of the potentiometric sensor apparatus.

19. The measuring arrangement as claimed in claim 18, further comprising:
  a second coating applied on a surface disposed within the process container and including a second calibration means, wherein the potentiometric sensor apparatus is movable relative to the second coating applied on the surface from a starting position, in which said measuring membrane of the sensor apparatus does not contact the second coating, into an end position, in which said measuring membrane of the sensor apparatus does contact the second coating for performing a calibration by means of the second calibration means.

20. A potentiometric sensor apparatus, comprising:
  a measuring half-cell including a measuring membrane comprising glass, the measuring membrane-having a leaching layer covered by a coating during dry storage of the potentiometric sensor apparatus, wherein the coating maintains the leaching layer, keeping the leaching layer functional during dry storage of the sensor apparatus, and wherein the coating includes a calibration buffer system adapted to enable calibration of the potentiometric sensor apparatus;
  at least one immersion region, which includes the measuring membrane and the coating;
  a reference half-cell; and
  a measurement circuit for registering a potential difference between said measuring half-cell and said reference half-cell,
  wherein the coating is embodied such that, in operation, upon immersion of at least a portion of the immersion region in a water-containing liquid and upon continued contact with the water-containing liquid, the coating at least partially dissolves from the measuring membrane.

21. The potentiometric sensor apparatus as claimed in claim 20, the calibration pH buffer system including at least one water soluble oligomer or polymer component, including an oligomer or polymer component that has at least one acid group, including a carbonyl acid, phosphoric acid, phosphonic acid or a sulfonic acid group.

* * * * *